United States Patent [19]

Ilmoniemi et al.

[11] Patent Number: 4,995,395
[45] Date of Patent: Feb. 26, 1991

[54] METHOD AND APPARATUS FOR LOCATION FINDING OF ELECTRODES PLACED ONTO THE BODY, PARTICULARLY TO THE HEAD

[75] Inventors: Risto Ilmoniemi; Seppo Ahlfors, both of Espoo, Finland

[73] Assignee: Neuromag OY, Espoo, Finland

[21] Appl. No.: 400,786

[22] Filed: Aug. 30, 1989

[30] Foreign Application Priority Data

Sep. 12, 1988 [FI] Finland ................................ 884187

[51] Int. Cl.$^5$ .......................... A61B 5/04; G01R 33/02
[52] U.S. Cl. .................................. 128/653 R; 324/207; 324/248
[58] Field of Search ...................... 128/653 R; 324/207, 324/247, 248

[56] References Cited

U.S. PATENT DOCUMENTS

| 4,613,817 | 9/1986 | Hoenig .............................. 324/248 |
| 4,731,582 | 3/1988 | Posseme et al. ..................... 324/247 |
| 4,736,751 | 4/1988 | Gevins et al. ...................... 128/732 |
| 4,793,355 | 12/1988 | Crum et al. ...................... 128/653 R |
| 4,812,812 | 3/1989 | Flowerdew et al. ................. 324/247 |

*Primary Examiner*—Lee S. Cohen
*Assistant Examiner*—Kevin Pontius

[57] ABSTRACT

A method and apparatus for finding the location of electrodes attached to a body, particularly to the head is provided with at least one first coil arranged in conjunction with each electrode. The coils of the electrodes form a coil group to be localized. A plurality of other coils are arranged in the vicinity of the electrodes so that the position of the coils is uniquely known. The second set of coils forms a fixed coil group. A magnetic field is induced in at least a part of either the first coil group or the second coil group. The set of coils not generating the magnetic field are used for detecting the induced magnetic field. The measured results from the group of coils acting as a magnetometer are used to determine the position of electrodes. Using this implementation, the positions of the electrodes can be determined in a quick and accurate manner.

9 Claims, 2 Drawing Sheets

METHOD AND APPARATUS FOR LOCATION FINDING OF ELECTRODES PLACED ONTO THE BODY, PARTICULARLY TO THE HEAD

The present invention relates to a method for the finding the location of electrodes placed on a body, particularly on a head.

The invention also concerns an apparatus applicable for the implementation of the method.

Conventionally, used in brain function diagnostics and research electrodes, which are attached to the scalp allowing the potential distribution of brain-function-induced electrical voltages to be measured on the scalp, are used in brain function diagnostics and research.

The electrodes are generally attached to standardized positions using, e.g., a tape measure for proper alignment. The deviation on placement accuracy is then typically in the order of 5 to 10 mm.

When a more accurate localization of the electrode's position is desired, a three-dimensional digitizer can be used, whereby each electrode is located by touching each placed electrode individually with the digitizer tip.

Another method is to record the head and the electrodes attached to it on a video tape or photographic film, allowing a later determination of the electrode locations.

The head shape can also be determined with the help of the three-dimensional digitizer by sliding the digitizer tip along the head contour or touching individual positions on the scalp. Photography is not applicable to this approach due the masking of head shape by hair.

The use of a tape measure is slow, inaccurate and also unreliable due to human errors in measuring.

The digitizer is slow in use and unreliable due to operator's errors.

Photography is hampered by the masking of a portion of the electrodes by hair or other visual obstacles In addition, the numerical interpretation of pictures is complicated.

Determination of head shape with the digitizer is laborious.

The present invention aims to overcome the disadvantages involved in the above-described techniques to achieve an entirely novel method for the localization of electrodes positions.

The invention is based on providing each electrode with one or several coils, allowing the electrode position and shape of the object to be determined by measuring the magnetic field induced by electrical current fed into the coils.

In addition to the coils, the system comprises a current source apparatus and an equipment for the measurement of magnetic field. Typically the system also comprises a computing apparatus, which determines the coordinates of the coils from the measured magnetic field values. The measurement equipment of magnetic field can consist of, for instance, one or several induction coils or a multichannel SQUID magnetometer. The SQUID magnetometer is specifically applicable in the case when the same person is subjected to both MEG and EEG measurements. The location finding of the electrodes can then be performed automatically in conjunction with the MEG registrations recorded from the subject.

In an advantageous implementation in accordance with the invention, three coils oriented in different directions and located at the same spatial point, are used to induce a magnetic field, which is then measured with the help of a multichannel brain-scanning magnetometer. The measured signal values are utilized for processing the signals to correspond to the situation as if the field-inducing transmitter coils were aligned orthogonally (this is necessary in case the coils are not already factory-aligned orthogonally). Then, the sum of the squares of these corrected field signals is not dependent on the orientation of the transmitter coils but only on their position with respect to the brain-scanning magnetometer. Three unknown components of the position vector can be determined if the magnetic field is measured at least from three different positions—necessitating the use of a magnetometer with at least three channels. The computation can be performed using a computer and a method for solving nonlinear equation groups.

More specifically, the method in accordance with the invention for finding the location of electrodes is characterized by providing each electrode with at least one first coil, so as to form a coil group to be localized; arranging a plurality of second coils in the vicinity of the electrodes, so that he position of the coils is uniquely known, so as to form a fixed cal group; inducing a magnetic field in at least part of the coils in one of the coil groups, whereby correspondingly the group of coils not participating in the generation of the magnetic fields act as a measuring magnetometer; and utilizing the measured results obtained from the coil group acting as the magnetometer to determine the positions of the electrodes.

Furthermore, the apparatus in accordance with the invention is characterized by at least one first coil arranged in each electrode, whereby the coils of the electrodes form a coil group to be localized; a plurality of second coils arranged in the vicinity of the electrodes so that the position of the coils is uniquely known, whereby the second group of coils forms a fixed coil group; a current device for inducing a magnetic field in at least part of the coils in either the coil group or the fixed coil group, whereby the coil group (B or A, respectively) not generating the magnetic field can be used for detecting the induced magnetic field; a measuring device, connected to the detecting coil group, for electronically receiving signals; and a data processing unit, connected to the measuring device for processing the received signal to determine the position of the electrodes.

The invention offers an automatic spatial location of the electrode ends on the skin of the head with a high accuracy, which is mandatory for, e.g., the interpretation of EEG signals. If several electrodes are used, the heads shape can be determined concurrently, which also provides support in the interpretation of the signals When several magnetometers are used simultaneously with the EEG measurement for the registration of MEG signals, these magnetometers can then be availed in the location of the electrodes, making a major portion of the location system equipment available as a "cost-free" option.

A preferred embodiment of the present invention utilizes the orthogonal orientation to dispose of the use of separate receiver coils managing only with the use of three transmitter coils, which are oriented in different directions. The transmitter coils can be fabricated small in size ($\leq 300$ mm$^3$), allowing their placement on the patient's head without causing complications in the placement of the brain-scanning magnetometer. Current is conducted in the coils via a twisted-pair, making it possible to place the current source away from the measurement site to avoid induced disturbances When using three orthogonally oriented transmitter coils, the computation of location is quick and reliable. With a carefully calibrated system, the location tolerance of approx. 1 mm can be attained.

The invention is next examined in detail with the help of the exemplifying embodiments illustrated in the attached drawings FIG. 1 shows diagrammatically a measurement setup in accordance with the invention.

FIG. 6b shows the dipole vectors and the directional vector of the receiver winding for the embodiment illustrated in FIG. 6a.

FIG. 6c shows the measurement situation with one dipole activated in the embodiment illustrated in FIG. 6a.

Figure 1:
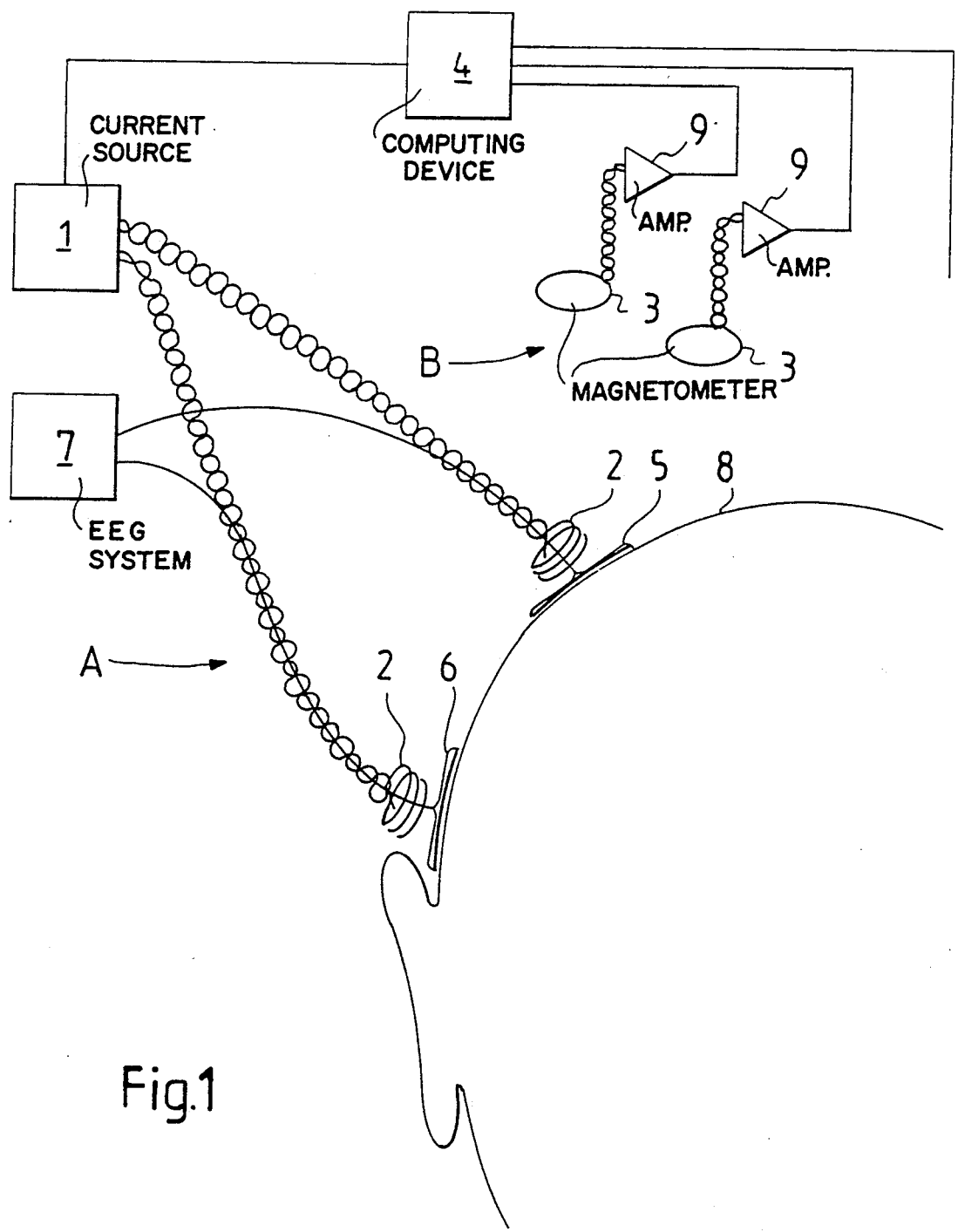

FIG. 1 shows the basic components of the apparatus required in the implementation of the method: A current source 1, a coil 2, a magnetometer 3 and a computing apparatus 4.

The current source 1 feeds current into each coil so that magnetic fields are induced by the coils and can be measured individually.

FIG. 1 illustrates the measurement setup for one channel. The EEG system of electronically (EEG-=electroencephalography) amplifies and records the brain-activity-evoked, time-dependent potential difference between the electrodes 5 and 6. The electrodes 5 and 6 are placed in ohmic contact with the skin 8 of the head. Since the potential difference to be measured is dependent on the placement of the electrodes to the head, the interpretation of the signals requires the positions of the electrodes be known. For location finding, each electrode has a coil 2 attached to it. The coil 2 attached to the electrode 5 is connected to a dedicated twisted pair of conductors. The group of coils formed by the coils 2 attached to the electrode 5 is herein called the coil group A to be localized. The current fed from the current source 1 to coil 2 induces a magnetic field with a known magnitude, which is measured with the help of magnetometer sensors 3, in which the signal is amplified with amplifiers 9. The coil group formed by the magnetometer sensors 3 is correspondingly herein called the fixed coil group B. The obtained measurement results are processed in a computing apparatus 4, which also can control the current feed from the current source 1. When several electrodes are to be localized, a practical approach to the measurement is to feed the current to each coil 2 of the electrodes 5 and 6 at different times.

Figure 2:
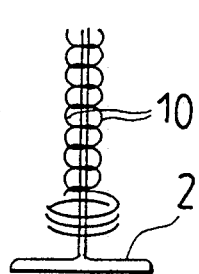
FIG. 2 shows diagrammatically a connection method for the coil.
Figure 3:
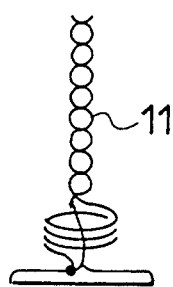
FIG. 3 shows diagrammatically another connection method for the coil.
Figure 4:
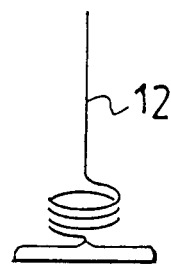
FIG. 4 shows diagrammatically a third connection method for the coil.

FIGS. 2, 3, and 4 illustrate three different current feed implementations, which provide for a simplified construction of the electrode with its coils. In the implementation shown in FIG. 2, a dedicated twisted pair 10 is routed to the coil 2, while the EEG lead is separate as in the implementation shown in FIG. 1. The described form of this construction offers the benefit, that the system complies with safety codes and poses no evident problems, since the insulated conductors of the current loop cannot come into galvanic contact with the skin.

FIG. 3 illustrates an implementation offering a reduced number of conductors by using the electrode lead 11 as the return lead of the current loop.

FIG. 4 illustrates an implementation in which the current is fed along the actual EEG lead 12, while the return lead of the current loop is provided by any of the other of the remaining electrode leads. If the coil is fabricated with a reasonably high number of turns, a sufficiently strong magnetic field is obtained with such a low current, which remains below the limits expressed in safety codes. Simultaneously, the field induced by the coil becomes high in magnitude in comparison with the fields created by the current loop leads and current passing through the head, allowing the coil's location to be computed using the assumption that the coil alone induces the measured field. It must be pointed out that also in EEG recording systems currently used a low-level current is fed through the head via the electrodes. This convention is because of the measurement of electrode resistances, and is of no nuisance or harm to the patient.

The magnetic field can be measured using, for instance, a magnetometer of the SQUID or induction coil type. The current amplitude and waveshape to be fed to the coil are selected so as to attain a maximally high signal-to-noise ratio during the measurement. It must be pointed out that when a coil is used as the sensor the measurement of magnetic field, in the mutual inductance of the electrode coil and the sensor coil is being measured Therefore, it is possible to interchange the functions of the coils so that the coils attached to the electrodes perform the measurement of magnetic field, which is created by coils placed at known positions.

If the diameter of the coil is small in relation to the distance between the closest magnetometer sensor, and simultaneously, the stray field created by the current feed leads, the induced magnetic field can be approximated using the equation of a magnetic dipole. The electrode position can then be computed by determining the position coordinates for such a magnetic dipole and the components for such a dipole moment vector that provide the best fit with the recorded measurement values. A possible method for this approach is the computation of the sum of least squares with the help of a computer.

Head shape and electrode positions can also be determined by using the electrode coils, and possibly also coils placed detached from the electrode coils, as transmitters and receivers in alternation. In the case of n coils the measurements can detect $n(n-1)$ mutual inductances. In order to be able to determine $5n$ unknown variables (since each axially symmetric coil has 3 position coordinates and two angles) it is required that $n(n-1) > 5n$, which gives the condition that $n > 6$.

Figure 5:
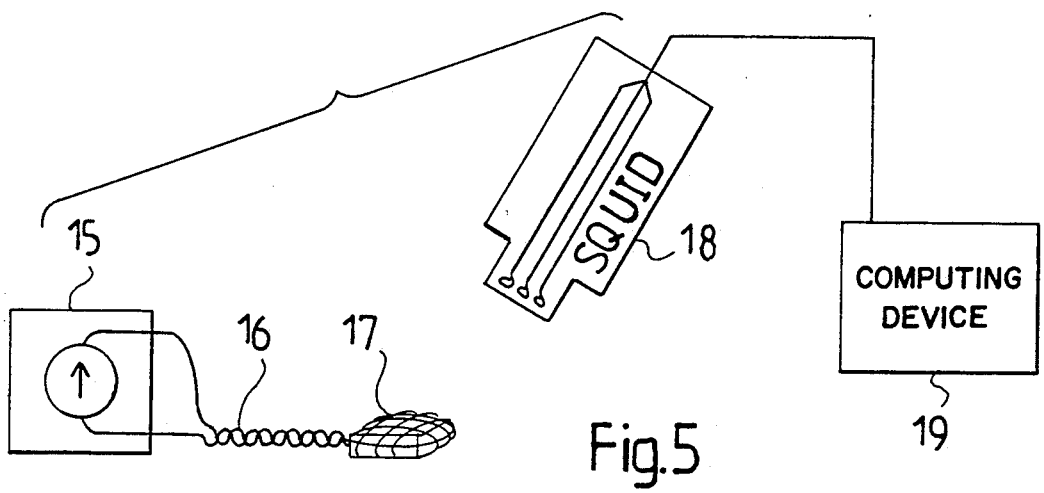
FIG. 5 shows an orthogonal measurement setup in accordance with the invention.

FIG. 5 illustrates a multicoil system applicable to location finding. The signal is routed from a current source 15 via a twisted pair 16 to three orthogonally oriented windings 17. The magnetic field induced by the windings 17 is measured with the help of a multichannel SQUID magnetometer 18 and the measurement results are processed with the help of a computing apparatus 19 to obtain the relative positions and orientations of the windings and the magnetometer.

Measurement by means of the system illustrated in FIG. 5 takes place as follows: Three or more triplet windings 17 are mounted to the patient's head. The winding axes are oriented in different directions, preferably orthogonally. An absolute orthogonality is not necessary, because if the orientations of winding axes are known, the corrections for orthogonally oriented field signals can be computed An essential presumption is that the triplet windings must have a common center point to make it possible to describe them with a model comprising of magnetic dipoles, which are placed to the center point and oriented in different directions.

Each coil is fed alternately with current from the current source 15 via the twisted pair 16. The magnetometer 18 is used for measuring a single component of the magnetic field, or alternatively, a singly sum or difference of field components from at least three different positions without moving the coils or the magnetometer.

On the basis of the measured signal values, the computing apparatus 19 can be used for computing the position of the triplet winding 17 in a coordinate system referenced to the magnetometer. The computations will take into account the directional deviations of the axes of windings 17 from absolutely orthogonal orientation. Next, signals of one magnetometer channel are processed to obtain the sum of squares of signals measured from three separate transmitters, whereby a positional signal, which is dependent only on the position but not on the orientation, is obtained. This desired positional information is determined with the help of a computing apparatus, e.g., a computer, by using a suitable solving method of a set of nonlinear equations, wherein the Marquardt method for instance is effective and reliable in the minimization of the sum of squares.

For a unique determination of the magnetometer position in relation to the head, at least three transmitter winding triplets of the above described type must be attached to the head.

Figure 6A:
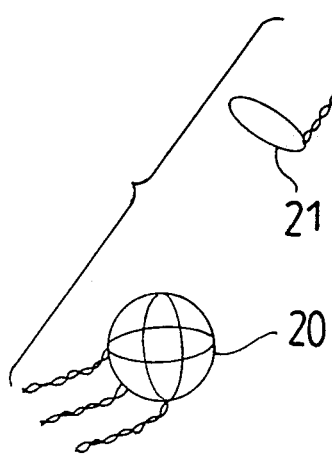
FIG. 6a shows a measurement setup in accordance with the invention having three orthogonal transmitter windings and a singe receiver winding.
Figure 6B:
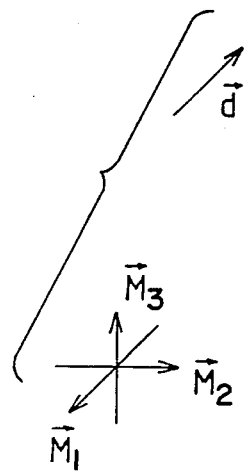
Figure 6C:
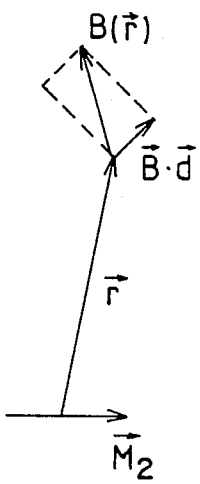

FIG. 6a shows three orthogonally oriented transmitter windings 20 and a single receiver winding 21. When the diameters of the windings are small in relation to the mutual spacing of the triplet from the receiver coil winding, the magnetic field of the transmitting coil can be approximated with the field of a magnetic dipole of a point source. Correspondingly, the receiver winding 21 can be assumed to measure the field in a single point. The dipole vectors in FIG. 6b are designated with symbols $\vec{M}_1$, $\vec{M}_2$ and $\vec{M}_3$, while the directional vector of the receiver winding is designated with the symbol d. Illustrated in FIG. 6c is the situation, in which one dipole of the system is activated. The relative positional vector from the transmitter to the receiver is designated as $\vec{r}$, the density vector of magnetic field as $\vec{B}(\vec{r})$ and the field component measured at the receiver coil $\vec{B}\cdot\vec{d}$.

In addition to the location finding of EEG electrodes, the above described method can be applied to the location finding of ECG and other electrodes as well as to the location finding and determination of contour shapes of other objects in, for instance, biomagnetic multichannel measurements such as those used in heart and lung scanning.

In the system described above, a generalized term coil (winding) has been used to denote the current loop component, which creates the measured magnetic field. In the interest of a simplified mechanical construction, the conventional electrodes with single-conductor leads should preferably be used as such for creating the magnetic field in such a manner that the current is conducted via the electrode and the head, while one or several of the other conductors act as the return leads.

What is claimed is:

1. A method for finding a location of electrodes placed on a head, comprising the steps of:
    (a) providing each electrode with at least one first coil, said at least one first coils forming a first coil group to be localized;
    (b) arranging a plurality of second coils in a vicinity of the electrodes, so that a position of the second coils is uniquely known, the second coils forming a fixed second coil group;
    (c) inducing a magnetic field in at least part of the coils in either the first coil group or the second coil group, whereby the coil group not generating the magnetic field acts as a measuring magnetometer; and
    (d) utilizing measured results obtained from the coil group acting as the magnetometer to determine the positions of the electrodes.

2. The method as claimed in claim 1, wherein the first coil group is used for inducing the magnetic field, while the fixed second coil group acts as the magnetometer.

3. The method as claimed in claim 1, further comprising the step of:
    (e) orthogonally orientating the coils with respect to each other.

4. The method as claimed in claim 1, wherein the position of the electrode is computed from results obtained with the magnetometers by determining the position coordinates of a magnetic dipole or set of dipoles as well as components of a dipole moment vector or set of vectors, which in combination provide a best fit with the measured results when using a summing method of least squares.

5. The method as claimed in claim 1, wherein the positions of the electrodes are determined by taking into account a deviation of an axis of a coil from a mutually orthogonal orientation and then summing squares of signal magnitudes measured from three different transmitters for one magnetometer channel, and using a Marquardt method for solving a set of nonlinear equations.

6. An apparatus for finding locations of electrodes attached to a head, comprising:
    a plurality of electrodes;
    at least one first coil attached to each electrode, said at least one first coils attached to the electrodes forming a first coil group to be localized;
    a plurality of second coils adapted to be arranged in a vicinity of the electrodes so that a position of said second coils is uniquely known, said second coils forming a fixed second coil group;
    current means for generating a magnetic field with either said first coil group or said second coil group, whereby said coil group not generating the magnetic field is used for detecting the induced magnetic field;
    measuring means electronically connected to said coil group detecting the induced magnetic field, for detecting a signal representing the induced magnetic field; and
    data processing means, connected to said measuring means, for processing said signal to determine the position of the electrodes.

7. The apparatus as claimed in claim 6, wherein said coil group detecting the induced magnetic field in a SQUID magnetometer.

8. The apparatus as claimed in claims 6 or 7, wherein said coil group generating the magnetic field is a coil combination having three coils which are oriented in different directions, while centers of said three coils essentially coincide at a single point.

9. The apparatus as claimed in claim 8, wherein said three coils are aligned orthogonally with respect to each other.

* * * * *